(12) United States Patent
Kim et al.

(10) Patent No.: US 9,271,988 B2
(45) Date of Patent: Mar. 1, 2016

(54) COMBINATION THERAPY COMPRISING A CDK4/6 INHIBITOR AND A P13K INHIBITOR FOR USE IN THE TREATMENT OF CANCER

(75) Inventors: Sunkyu Kim, Cambridge, MA (US); Shivang Doshi, Brookline, MA (US); Kristy Haas, Brighton, MA (US); Steven Kovats, Wilmington, MA (US); Alan Xizhong Huang, Southborough, MA (US); Yan Chen, Lexington, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/124,753

(22) PCT Filed: Jul. 2, 2012

(86) PCT No.: PCT/US2012/045199
§ 371 (c)(1),
(2), (4) Date: Dec. 9, 2013

(87) PCT Pub. No.: WO2013/006532
PCT Pub. Date: Jan. 10, 2013

(65) Prior Publication Data
US 2014/0107114 A1    Apr. 17, 2014

Related U.S. Application Data

(60) Provisional application No. 61/503,642, filed on Jul. 1, 2011.

(51) Int. Cl.
| | | |
|---|---|---|
| *A61K 31/519* | (2006.01) | |
| *A61K 31/5377* | (2006.01) | |
| *C07D 487/02* | (2006.01) | |
| *A61K 31/4439* | (2006.01) | |
| *A61K 45/06* | (2006.01) | |

(52) U.S. Cl.
CPC ......... *A61K 31/5377* (2013.01); *A61K 31/4439* (2013.01); *A61K 31/519* (2013.01); *A61K 45/06* (2013.01)

(58) Field of Classification Search
CPC . A61K 31/519; A61K 31/5377; C07D 487/02
USPC ............... 544/242, 253, 280; 514/256, 258.1
See application file for complete search history.

(56) References Cited

U.S. PATENT DOCUMENTS

| | | | | |
|---|---|---|---|---|
| 8,586,576 B2* | 11/2013 | Guzi et al. | ................ | 514/218 |
| 8,673,924 B2* | 3/2014 | Guzi et al. | ................ | 514/259.3 |

FOREIGN PATENT DOCUMENTS

| | | |
|---|---|---|
| WO | 2007/084786 | 7/2007 |
| WO | 2010/020675 | 2/2010 |
| WO | 2010/029082 | 3/2010 |

OTHER PUBLICATIONS

Borland et al (2011): STN International HCAPLUS database, Columbus (OH), accession No. : 2011: 1337222.*
Miller et al, "ER[alpha]-dependent E2F transcription . . . ", Cancer Discovery, vol. 1, No. 4, pp. 338-351, 2011.
Witters et al, "The antiproliferative effect of the combination of the cyclin-dependent kinase . . . ", AACR Meeting, vol. 45, p. 123, 2004.
Carlson et al, "Flavopindol induces G1 arrest with inhibition . . . ", Cancer Research, vol. 56, No. 13, pp. 2973-2978, 1996.
Chunrong et al, "The lethal effects of pharmacological . . . ", vol. 63, No. 8, pp. 1822-1833, 2003.

* cited by examiner

*Primary Examiner* — Golam M M Shameem
(74) *Attorney, Agent, or Firm* — Jennifer C Chapman

(57) ABSTRACT

A combination of a CDK4/6 inhibitor and a P3Kinase inhibitor for the treatment of cancer.

4 Claims, 4 Drawing Sheets

COMBINATION THERAPY COMPRISING A CDK4/6 INHIBITOR AND A PI3K INHIBITOR FOR USE IN THE TREATMENT OF CANCER

FIELD OF THE DISCLOSURE

A combination of a cyclin dependent kinase 4/6 (CDK4/6) inhibitor and a Phosphatidylinositol 3-Kinase (PI3Kinase) inhibitor for the treatment of solid tumors and hematological malignancies. This disclosure also relates to the use of the combination thereof, in the management of hyperproliferative diseases like cancer.

RELATED BACKGROUND ART

Cyclin dependent kinase 4/6 (CDK4/6) inhibitors are described in, for example, WO2007/140222 and WO2010/020675, which are hereby incorporated by reference in entirety.

Phosphatidylinositol 3-Kinase (PI3Kinase) inhibitors are described in, for example, WO2004/048365, WO2007/084786, WO2004/096797, WO2010/029082, WO2006/122806 which is hereby incorporated by reference in entirety.

BRIEF SUMMARY OF THE DISCLOSURE

The disclosure provides a combination comprising a first agent that inhibits the CDK4/6 pathway and a second agent that inhibits PI3Kinase. In another aspect, the disclosure provides combinations including pharmaceutical compositions comprising a therapeutically effective amount of a first agent that inhibits CDK4/6, a second agent that inhibits PI3Kinase, and a pharmaceutically acceptable carrier.

Furthermore, the present disclosure provides for the use of a therapeutically effective amount of a combination comprising a first agent that inhibits the CDK4/6 pathway and a second agent that inhibits PI3Kinase, or a pharmaceutically acceptable salt or pharmaceutical composition thereof, in the manufacture of a medicament for treating cancer.

The present disclosure has a therapeutic use in the treatment of various proliferative diseases.

The above combinations and compositions can be administered to a system comprising cells or tissues, as well as a human patient or and animal subject.

In one embodiment, the first agent that inhibits the CDK4/6 pathway is Compound A which is 7-Cyclopentyl-2-(5-piperazin-1-yl-pyridin-2-ylamino)-7H-pyrrolo[2,3-d]pyrimidine-6-carboxylic acid dimethylamide or pharmaceutically acceptable salt(s) thereof. Compound A is described by Formula A:

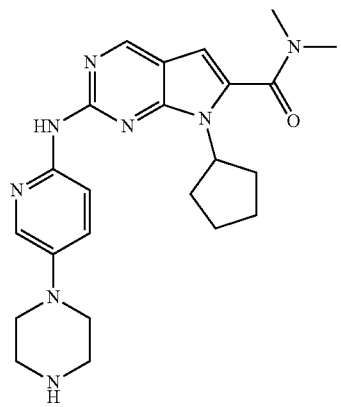

Formula A or pharmaceutically acceptable salt(s) thereof.

In another embodiment, the second agent that inhibits PI3Kinase is Compound B1 described by Formula B1:

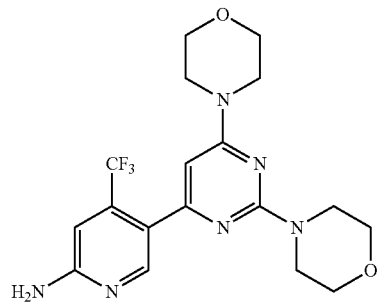

Formula B1 or pharmaceutically acceptable salt(s) thereof.

Compound B1 has been described with several names, such as 4-(trifluoromethyl)-5-(2,6-dimorpholinopyrimidin-4-yl)pyridin-2-amine; 5-(2,6-di-morpholin-4-yl-pyrimidin-4-yl)-4-trifluoromethyl-pyridin2-ylamine; 5-(2,6-Di-4-morpholinyl-4-pyrimidinyl)-4-trifluoromethylpyridin-2-amine; or CAS name 5-(2,6-di-4-morpholinyl-4-pyrimidinyl)-4-(trifluoromethyl)-2-pyrimidinamine.

In another embodiment, the second agent that inhibits PI3Kinase is Compound B2 described by Formula B2:

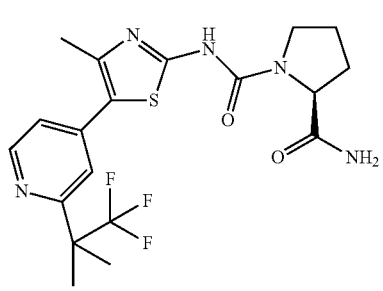

Formula B2 or pharmaceutically acceptable salt(s) thereof.

Compound B2 is known as (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide).

BRIEF DESCRIPTION OF THE DRAWINGS

FIG. 4 illustrates the results when the combination of Compound A and Compound B2, is used to treat T47-D cells. The

DETAILED DESCRIPTION OF THE DISCLOSURE

Figure 1:
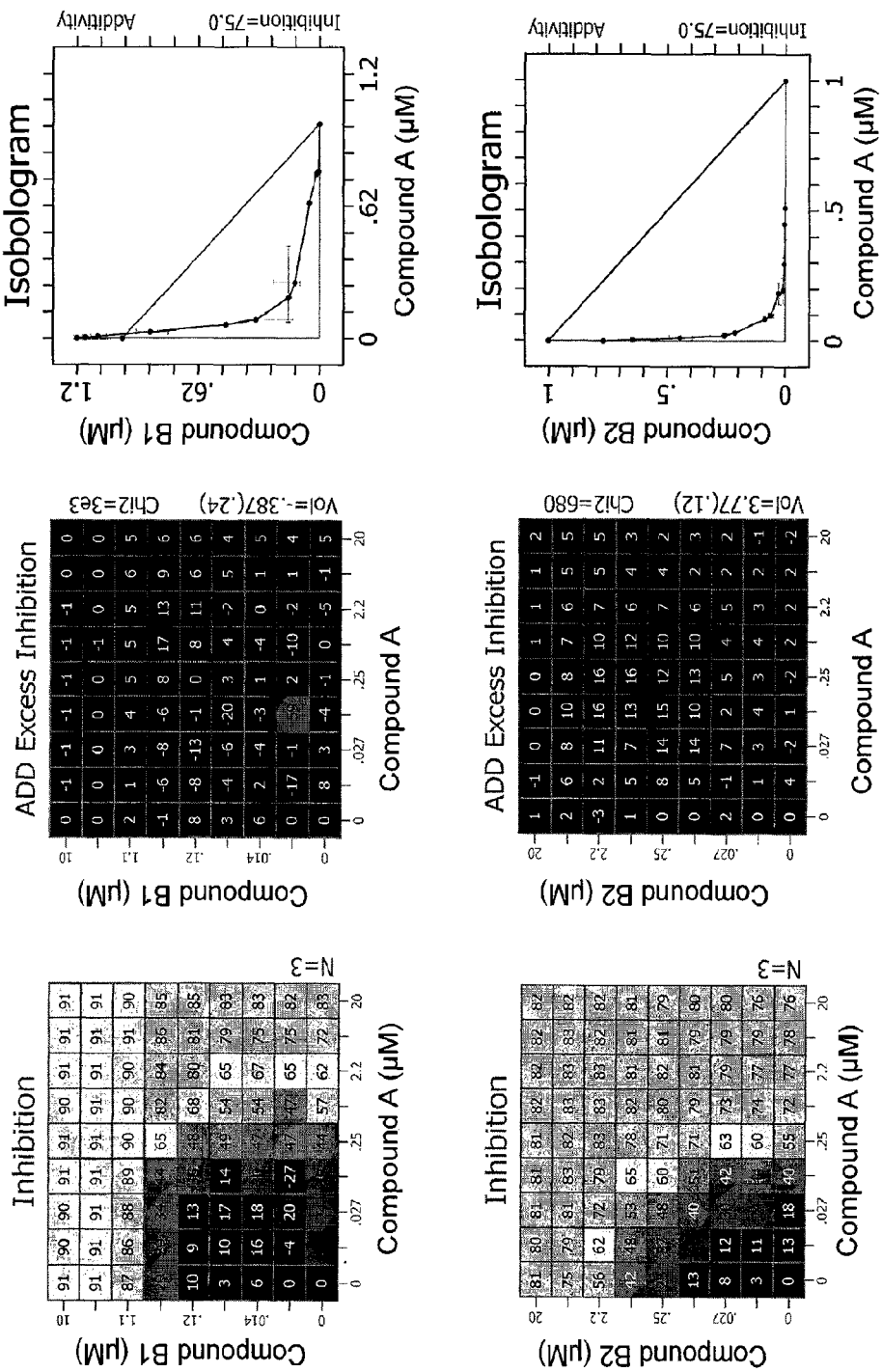
FIG. 1 illustrates the results when the combination of Compound A and Compound B1 or Compound B2, is used to treat MDA-MB-453 cells. The resulting inhibition values were used by CHALICE software to generate Inhibition and ADD Excess Inhibition matrices, as well as the isobolograms.

The disclosure provides a combination comprising a first agent that inhibits the CDK4/6 pathway and a second agent that inhibits PI3Kinase. In another aspect, the disclosure provides combinations including pharmaceutical compositions comprising a therapeutically effective amount of a first agent that inhibits CDK4/6, a second agent that inhibits PI3Kinase, and a pharmaceutically acceptable carrier.

Furthermore, the present disclosure provides for the use of a therapeutically effective amount of a combination comprising a first agent that inhibits the CDK4/6 pathway and a second agent that inhibits PBKinase, or a pharmaceutically acceptable salt or pharmaceutical composition thereof, in the manufacture of a medicament for treating cancer.

The present disclosure has a therapeutic use in the treatment of various proliferative diseases.

The above combinations and compositions can be administered to a system comprising cells or tissues, as well as a human patient or and animal subject.

In one embodiment, the first agent that inhibits the CDK4/6 pathway is Compound A which is 7-Cyclopentyl-2-(5-piperazin-1-yl-pyridin-2-ylamino)-7H-pyrrolo[2,3-d]pyrimidine-6-carboxylic acid dimethylamide or pharmaceutically acceptable salt(s) thereof. Compound A is described by Formula A:

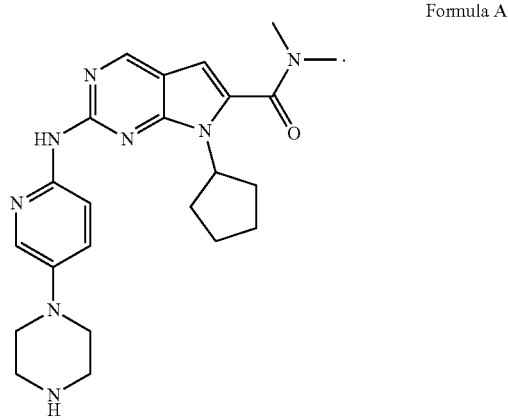 [SMILES: CN(C)C(=O)c1cc2cnc(Nc3ccc(N4CCNCC4)cn3)nc2n1C1CCCC1]

Formula A

In another embodiment, the second agent that inhibits PI3Kinase is Compound B1 described by Formula B1:

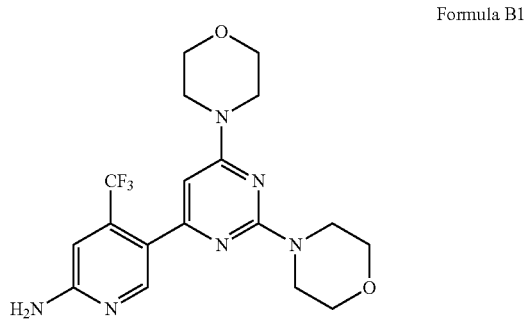 [SMILES: Nc1cc(C(F)(F)F)c(-c2cc(N3CCOCC3)nc(N3CCOCC3)n2)cn1]

Formula B1 or pharmaceutically acceptable salt(s) thereof.

Compound B1 has been described with several names, such as 4-(trifluoromethyl)-5-(2,6-dimorpholinopyrimidin-4-yl)pyridin-2-amine; 5-(2,6-di-morpholin-4-yl-pyrimidin-4-yl)-4-trifluoromethyl-pyridin2-ylamine; 5-(2,6-Di-4-morpholinyl-4-pyrimidinyl)-4-trifluoromethylpyridin-2-amine; or CAS name 5-(2,6-di-4-morpholinyl-4-pyrimidinyl)-4-(trifluoromethyl)-2-pyrimidinamine.

In another embodiment, the second agent that inhibits PI3 Kinase is Compound B2 described by Formula B2:

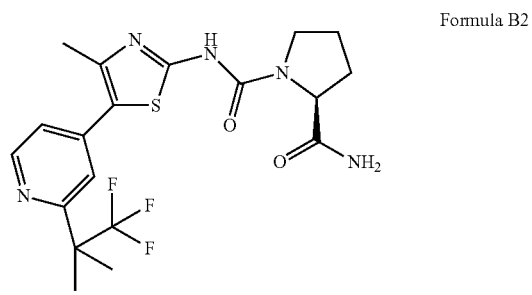 [SMILES: Cc1nc(NC(=O)N2CCC[C@H]2C(N)=O)sc1-c1ccnc(C(C)(C)C(F)(F)F)c1]

Formula B2 or pharmaceutically acceptable salt(s) thereof.

Compound B2 is known as (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide).

In another embodiment, the present disclosure includes a method of treating a hyperproliferative disease, preferably cancer. The compounds of the present disclosure inhibitors of CDK4/6 and PI3K, and therefore may be capable of treating diseases wherein the underlying pathology is (at least in part) mediated by activated CDK4/6 and/or PI3K pathway. Such diseases include cancer and other diseases in which there is a disorder of cell proliferation, apoptosis, or differentiation.

Thus the combination of the present disclosure may be useful in the treatment of RB+ve (retinoblastoma protein positive) tumours, including tumours harbouring activating mutations in Ras, Raf, Growth Factor Receptors, PI3K, or over-expression of Growth Factor Receptors, or inactivation of p16. The compounds of the present disclosure may also be useful in the treatment of tumours with amplifications of CDK4 and CDK6 genes as well as, tumours over-expressing cyclin partners of the cyclin dependent kinases. The compounds of the present disclosure may also be useful in the treatment of RB−ve tumours.

The combination of the present disclosure may also be useful in the treatment tumours with genetic aberrations that activate the CDK4/6 kinase activity. These include, but are not limited to, cancers with D-cyclin translocations such as mantle cell lymphoma and multiple myeloma, D-cyclin amplifications such as breast cancer and squamous cell esophageal cancer, CDK4 amplifications such as liposarcoma, CDK6 amplifications or overexpressions such as T-cell lymphoma and p16 inactivation such as melanoma, non-small cell lung cancer and pancreatic cancer.

The combination of the present disclosure may be useful in the treatment of cancers that have genetic aberrations in the upstream regulators of D-cyclins, where the defect results in an increase of D-cyclins abundance, can also be considered for treatment. These include, but are not limited to, acute myeloid leukemia with FLT3 activation, breast cancers with Her2/neu overexpression, ER dependency or triple negative phenotype, colon cancers with activating mutations of the MAPK, PI3K or WNT pathway, melanomas with activating mutations of MAPK pathway, non small cell lung cancers with activating aberrations of EGFR pathway and pancreatic cancers with activating aberrations of MAPK pathway including K-Ras mutations.

The combination of the present disclosure may be useful in the treatment of cancers that have activating mutations of PI3K. These include, but not limited to, breast cancer, endometrium cancer, urinary track cancer, melanoma, colon cancer, stomach cancer, cervical cancer, prostate cancer and ovarian cancer.

Examples of cancers which may be treated with a compound of the present disclosure include but are not limited to, carcinoma, for example a carcinoma of the bladder, breast, colon (e.g. colorectal carcinomas such as colon adenocarcinoma and colon adenoma), kidney, epidermis, liver, lung (e.g. adenocarcinoma, small cell lung cancer and non-small cell lung carcinomas), oesophagus, gall bladder, ovary, pancreas (e.g. exocrine pancreatic carcinoma), stomach, cervix, thyroid, nose, head and neck, prostate, and skin (e.g. squamous cell carcinoma). Other examples of cancers that may be treated with a compound of the present disclosure include hematopoietic tumours of lymphoid lineage (e.g. leukemia, acute lymphocytic leukemia, mantle cell lymphoma, chronic lymphocytic leukaemia, B-cell lymphoma (such as diffuse large B cell lymphoma), T-cell lymphoma, multiple myeloma, Hodgkin's lymphoma, non-Hodgkin's lymphoma, hairy cell lymphoma, and Burkett's lymphoma; hematopoietic tumours of myeloid lineage, for example acute and chronic myelogenous leukemias, myelodysplastic syndrome, and promyelocytic leukemia. Other cancers include thyroid follicular cancer; a tumour of mesenchymal origin, for example fibrosarcoma or habdomyosarcoma; a tumour of the central or peripheral nervous system, for example astrocytoma, neuroblastoma, glioma or schwannoma; neuroendocrine cancer; melanoma; prostate cancer; ovarian cancer; rhabdoid cancer; seminoma; teratocarcinoma; osteosarcoma; xeroderma pigmentosum; retinoblastoma; keratoctanthoma; thyroid follicular cancer; and Kaposi's sarcoma.

One group of cancers includes human breast cancers (e.g. ER positive breast cancer, Her2 positive breast cancer, PI3K mutated breast cancer, primary breast tumours, node-negative breast cancer, invasive duct adenocarcinomas of the breast, non-endometrioid breast cancers); and endometrial cancers. Another sub-set of cancers wherein compounds having CDK4/6 and/or PI3K inhibitory activity may be of particular therapeutic benefit comprises glioblastoma multiforme, T cell ALL, sarcomas, familial melanoma and melanoma.

The combination of the present disclosure could also be useful in the treatment of viral infections, for example herpes virus, pox virus, Epstein-Barr virus, Sindbis virus, adenovirus, HIV, HPV, HCV and HCMV; prevention of AIDS development in HIV-infected individuals; chronic inflammatory diseases, for example systemic lupus erythematosus, autoimmune mediated glomerulonephritis, rheumatoid arthritis, psoriasis, inflammatory bowel disease, and autoimmune diabetes mellitus; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anemia and aplastic anemia; degenerative diseases of the musculoskeletal system, for example, osteoporosis and arthritis, aspirin-senstive rhinosinusitis, cystic fibrosis, multiple sclerosis, kidney diseases, ophthalmic diseases including age related macular degeneration, uveitis, and cancer pain.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition/symptom in the host.

"Agent" refers to all materials that may be used to prepare pharmaceutical and diagnostic compositions, or that may be compounds, nucleic acids, polypeptides, fragments, isoforms, variants, or other materials that may be used independently for such purposes, all in accordance with the present disclosure.

The present disclosure includes all pharmaceutically acceptable isotopically-labeled compounds of the disclosure, i.e. compounds of Formula (I), wherein one or more atoms are replaced by atoms having the same atomic number, but an atomic mass or mass number different from the atomic mass or mass number usually found in nature.

Examples of isotopes suitable for inclusion in the compounds of the disclosure comprises isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of Formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of Formula (I) can generally be prepared by conventional techniques known to those skilled in the art or by processes analogous to those described in the accompanying Examples and Preparations using an appropriate isotopically-labeled reagents in place of the non-labeled reagent previously employed.

Compound A can be synthesized, for example, as described in WO2010/020675 or PCT/US2011/032062.

Compound B1 can be synthesized, for example, as described in WO2007/084786.

Compound B2 can be synthesized, for example, as described in WO2010/029082.

EXAMPLES

Example 1

Potential synergistic interactions between Compound A and Compound B1 or B2 combinations were assessed relative to the Loewe additivity model using CHALICE software, via a synergy score calculated from the differences between the observed and Loewe model values across the response matrix. Briefly, 9 titrating concentration ranging from 20 µM diluted serially three folds for Compound A and 10 µM diluted serially 3 folds for Compound B1 or B2, including 0 µM, were used. In a 96 well plate, the 9 concentration points for each agent were mixed in a matrix format, generating 81 combinations. This plate was used to treat MDA-MB-453 cells, and the resulting inhibition values were used by CHALICE software to generate Inhibition and ADD Excess Inhibition matrices, as well as the isobolograms. A more detailed explanation of the technique and calculation can be found in Lehar et al. "Synergistic drug combinations improve therapeutic selectivity", $Nat.\ Biotechnol.$ 2009, July; 27(7), 659-666, which is hereby incorporated by reference.

As illustrated by FIG. 1, inhibition matrix shows the actual inhibition observed by the CTG assay at the respective concentrations of the compounds. ADD Excess inhibition shows the excess inhibition observed over the inhibition predicted by the Loewe additivity model. In addition to the matrices, one can use isobolograms to observe synergy. The inhibition level for each isobologram was chosen manually so as to observe the best synergistic effects. Isobologram was generated with Compound A concentrations shown on the x-axis and Compound B1 or B2 concentrations shown on the y-axis. A straight line connecting the Compound A and the Compound B1 or B2 concentrations which produce the chosen level of inhibition represented growth inhibitions that were strictly additive for the combinations. Plots placed below the line of additivity (more growth inhibition) represented synergistic growth inhibitions, while plots above the line of additivity (less growth inhibition) represented antagonistic growth inhibitions.

Synergic interaction is observed for the combination of Compound A and Compound B1 or B2 in the MDA-MB-453 cells.

Example 2

Potential synergistic interactions between Compound A and Compound B1 or B2 combinations were assessed relative to the Loewe additivity model using CHALICE software, via a synergy score calculated from the differences between the observed and Loewe model values across the response matrix. Briefly, 9 titrating concentration ranging from 20 µM diluted serially three folds for Compound A and 20 µM diluted serially 3 folds for Compound B1 or B2, including 0 µM, were used. In a 96 well plate, the 9 concentration points for each agent were mixed in a matrix format, generating 81 combinations. This plate was used to treat breast cancer HCT-116 cells, and the resulting inhibition values were used by CHALICE software to generate Inhibition and ADD Excess Inhibition matrices, as well as the isobolograms. A more detailed explanation of the technique and calculation can be found in Lehar et al. "Synergistic drug combinations improve therapeutic selectivity", $Nat.\ Biotechnol.$ 2009, July; 27(7), 659-666, which is hereby incorporated by reference.

Figure 2:
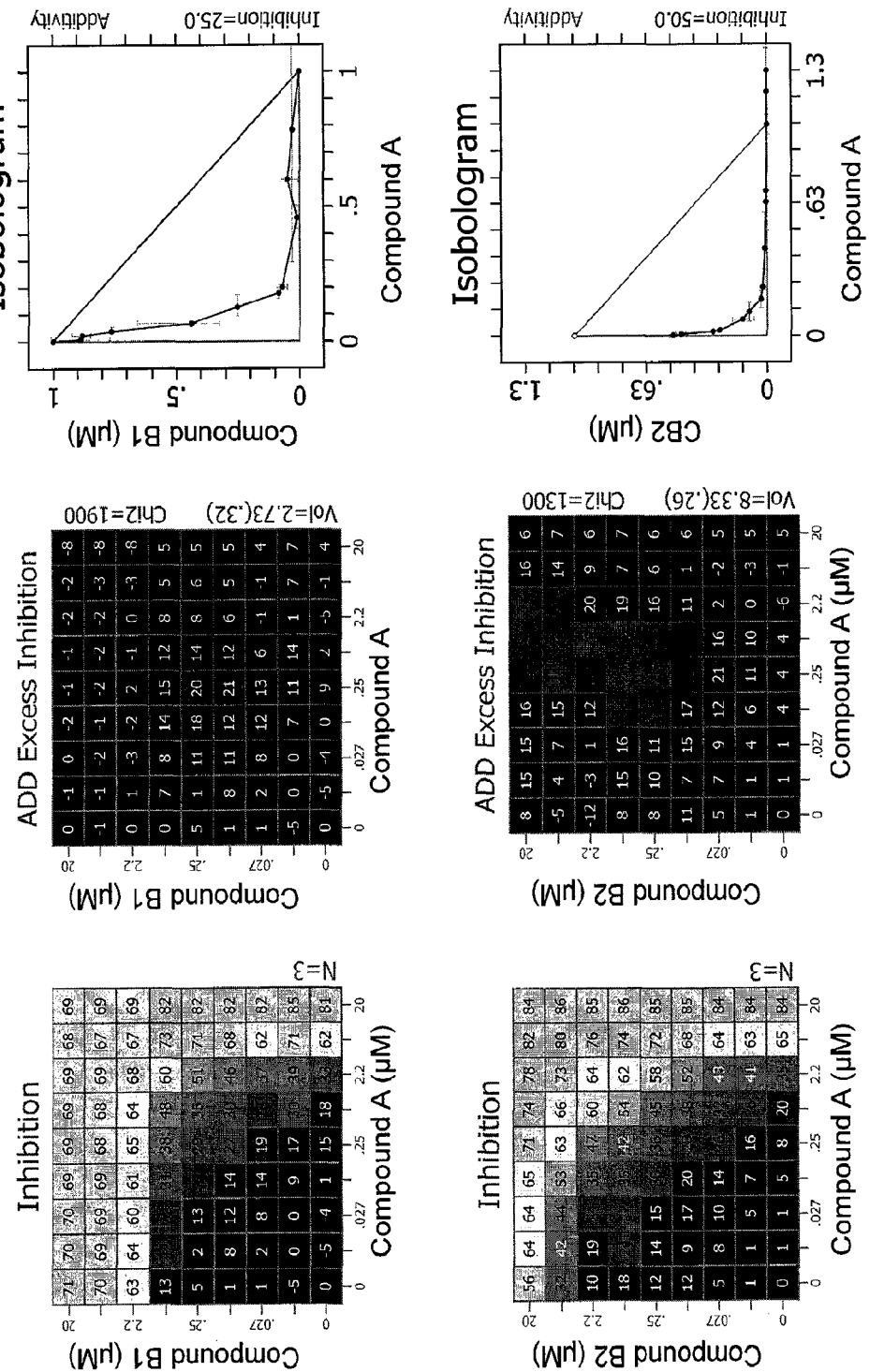
FIG. 2 illustrates the results when the combination of Compound A and Compound B1 or Compound B2, is used to treat HCT-116 cells. The resulting inhibition values were used by CHALICE software to generate Inhibition and ADD Excess Inhibition matrices, as well as the isobolograms.

As illustrated by FIG. 2, inhibition matrix shows the actual inhibition observed by the CTG assay at the respective concentrations of the compounds. ADD Excess inhibition shows the excess inhibition observed over the inhibition predicted by the Loewe additivity model. In addition to the matrices, one can use isobolograms to observe synergy. The inhibition level for each isobologram was chosen manually so as to observe the best synergistic effects. Isobologram was generated with Compound A concentrations shown on the x-axis and Compound B1 or B2 concentrations shown on the y-axis. A straight line connecting the Compound A and the Compound B1 or B2 concentrations which produce the chosen level of inhibition represented growth inhibitions that were strictly additive for the combinations. Plots placed below the line of additivity (more growth inhibition) represented synergistic growth inhibitions, while plots above the line of additivity (less growth inhibition) represented antagonistic growth inhibitions.

Synergic interaction is observed for the combination of Compound A and Compound B1 or B2 in the HCT-116 cells.

Example 3

Potential synergistic interactions between Compound A and Compound B1 or B2 combinations were assessed relative to the Loewe additivity model using CHALICE software, via a synergy score calculated from the differences between the observed and Loewe model values across the response matrix. Briefly, 9 titrating concentration ranging from 20 µM diluted serially three folds for Compound A and 20 µM diluted serially 3 folds for Compound B1 or B2, including 0 µM, were used. In a 96 well plate, the 9 concentration points for each agent were mixed in a matrix format, generating 81 combinations. This plate was used to treat ER positive breast cancer MCF-7 cells, and the resulting inhibition values were used by CHALICE software to generate Inhibition and ADD Excess Inhibition matrices, as well as the isobolograms. A more detailed explanation of the technique and calculation can be found in Lehar et al. "Synergistic drug combinations improve therapeutic selectivity", $Nat.\ Biotechnol.$ 2009, July; 27(7), 659-666, which is hereby incorporated by reference.

Figure 3:
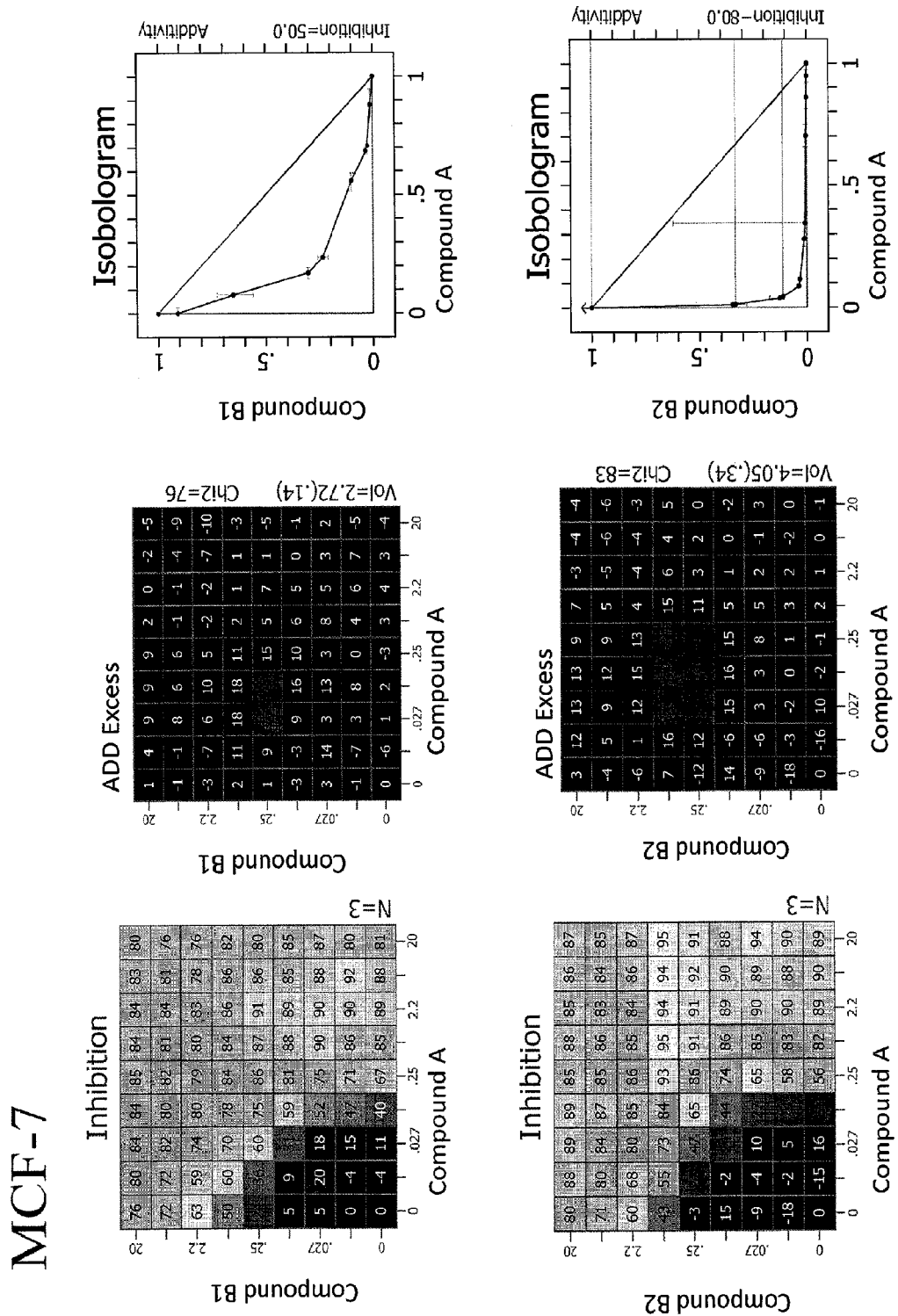
FIG. 3 illustrates the results when the combination of Compound A and Compound B1 or Compound B2, is used to treat MCF-7 cells. The resulting inhibition values were used by CHALICE software to generate Inhibition and ADD Excess Inhibition matrices, as well as the isobolograms.

As illustrated by FIG. 3, inhibition matrix shows the actual inhibition observed by the BrdU assay at the respective concentrations of the compounds. ADD Excess inhibition shows the excess inhibition observed over the inhibition predicted by the Loewe additivity model. In addition to the matrices, one can use isobolograms to observe synergy. The inhibition level for each isobologram was chosen manually so as to observe the best synergistic effects. Isobologram was generated with Compound A concentrations shown on the x-axis and Compound B1 or B2 concentrations shown on the y-axis. A straight line connecting the Compound A and the Compound B1 or B2 concentrations which produce the chosen level of inhibition represented growth inhibitions that were strictly additive for the combinations. Plots placed below the line of additivity (more growth inhibition) represented synergistic growth inhibitions, while plots above the line of additivity (less growth inhibition) represented antagonistic growth inhibitions.

Synergic interaction is observed for the combination of Compound A and Compound B1 or B2 in the MCF-7 cells.

Example 4

Potential synergistic interactions between Compound A and Compound B2 combinations were assessed relative to the Loewe additivity model using CHALICE software, via a synergy score calculated from the differences between the observed and Loewe model values across the response matrix. Briefly, 9 titrating concentration ranging from 20 µM diluted serially three folds for Compound A and 20 µM diluted serially 3 folds for Compound B2, including 0 µM, were used. In a 96 well plate, the 9 concentration points for each agent were mixed in a matrix format, generating 81 combinations. This plate was used to treat ER positive breast cancer T47-D cells, and the resulting inhibition values were used by CHALICE software to generate Inhibition and ADD Excess Inhibition matrices, as well as the isobolograms. A more detailed explanation of the technique and calculation can be found in Lehar et al. "Synergistic drug combinations improve therapeutic selectivity", *Nat. Biotechnol.* 2009, July; 27(7), 659-666, which is hereby incorporated by reference.

Figure 4:
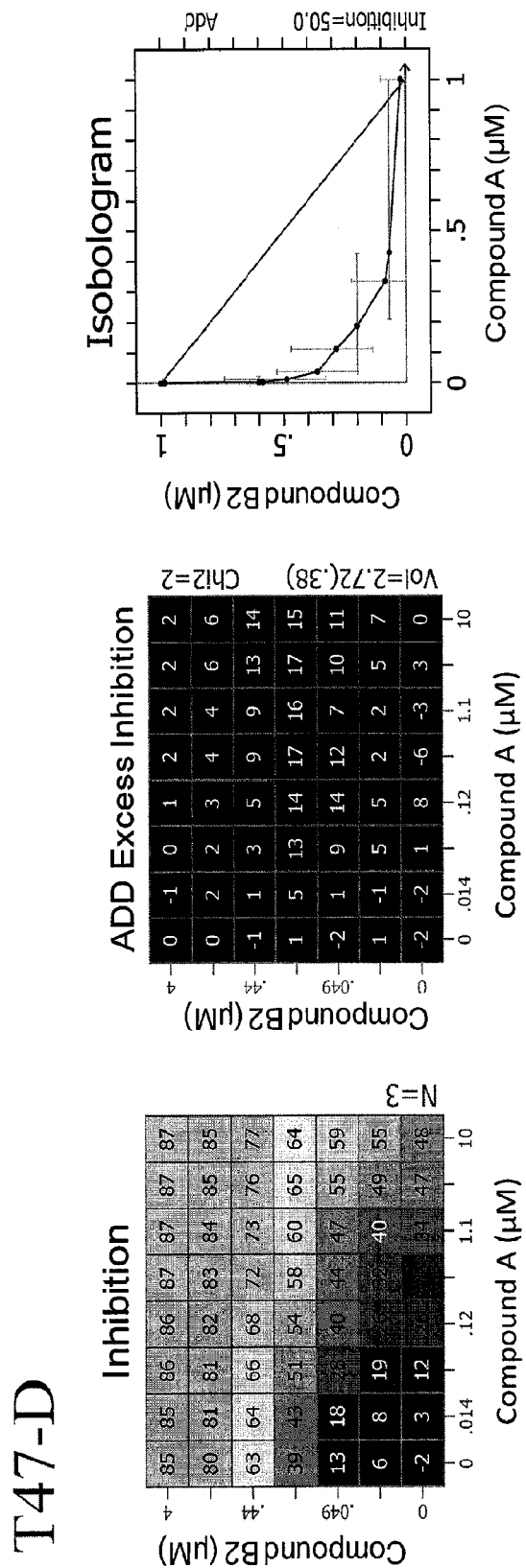

As illustrated by FIG. 4, inhibition matrix shows the actual inhibition observed by the BrdU assay at the respective concentrations of the compounds. ADD Excess inhibition shows the excess inhibition observed over the inhibition predicted by the Loewe additivity model. In addition to the matrices, one can use isobolograms to observe synergy. The inhibition level for each isobologram was chosen manually so as to observe the best synergistic effects. Isobologram was generated with Compound A concentrations shown on the x-axis and Compound B2 concentrations shown on the y-axis. A straight line connecting the Compound A and the Compound B2 concentrations which produce the chosen level of inhibition represented growth inhibitions that were strictly additive for the combinations. Plots placed below the line of additivity (more growth inhibition) represented synergistic growth inhibitions, while plots above the line of additivity (less growth inhibition) represented antagonistic growth inhibitions.

Synergic interaction is observed for the combination of Compound A and Compound B2 in the T47-D cells.

What is claimed is:

1. A combination comprising a first agent that is a cyclin dependent kinase 4 or cyclin dependent kinase 6 (CDK4/6) inhibitor and a second agent that is a PI3Kinase inhibitor.

2. The combination of claim 1 wherein the first agent is Compound A described by Formula A:

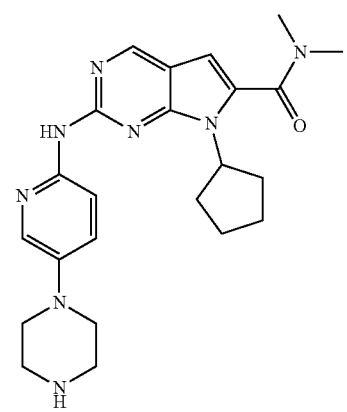

Formula A or a pharmaceutically acceptable salt thereof.

3. The combination of claim 1, wherein the second agent is Compound B1 described by Formula B1:

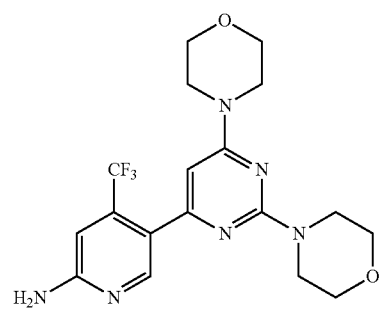

Formula B1 or a pharmaceutically acceptable salt thereof.

4. The combination of claim 1, wherein the second agent is Compound B2 described by Formula B2:

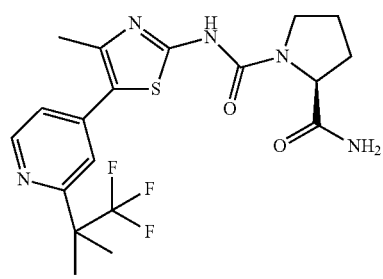

Formula B2 or a pharmaceutically acceptable salt thereof.

* * * * *